United States Patent
Lin et al.

(10) Patent No.: US 8,877,022 B2
(45) Date of Patent: Nov. 4, 2014

(54) BIOSENSOR

(75) Inventors: Shiming Lin, Taipei (TW); Bor-Ching Sheu, Tainan (TW); Luan-Yin Chang, Taipei (TW); Chih-Chen Lin, Kaohsiung County (TW)

(73) Assignee: National Taiwan University, Taipei (TW)

( * ) Notice: Subject to any disclaimer, the term of this patent is extended or adjusted under 35 U.S.C. 154(b) by 509 days.

(21) Appl. No.: 13/165,464

(22) Filed: Jun. 21, 2011

(65) Prior Publication Data

US 2012/0329037 A1 Dec. 27, 2012

(51) Int. Cl.
*G01N 27/327* (2006.01)
*G01N 33/543* (2006.01)

(52) U.S. Cl.
CPC ........ *G01N 33/5438* (2013.01); *G01N 27/3276* (2013.01)
USPC .......................... 204/400; 435/287.1; 435/7.9

(58) Field of Classification Search
USPC .......... 205/792, 775, 416; 257/40; 435/287.1, 435/7.9; 436/501; 422/59
See application file for complete search history.

(56) References Cited

U.S. PATENT DOCUMENTS

| | | |
|---|---|---|
| 5,491,097 A | 2/1996 | Ribi et al. |
| 5,571,568 A | 11/1996 | Ribi et al. |
| 5,622,872 A | 4/1997 | Ribi |
| 5,776,672 A | 7/1998 | Hashimoto et al. |
| 5,972,692 A | 10/1999 | Hashimoto et al. |
| 8,101,429 B2 * | 1/2012 | Krauth et al. ................. 436/514 |
| 2003/0187182 A1 | 10/2003 | Cha et al. |
| 2004/0195563 A1 | 10/2004 | Bao et al. |
| 2005/0208579 A1 | 9/2005 | Cha et al. |
| 2006/0243969 A1 | 11/2006 | Bao et al. |
| 2007/0207465 A1 * | 9/2007 | Kayyem et al. ................... 435/6 |
| 2009/0294305 A1 | 12/2009 | Bekki et al. |

FOREIGN PATENT DOCUMENTS

| | | |
|---|---|---|
| DE | 102 26 945 A1 | 1/2004 |
| EP | 1 347 463 A2 | 9/2003 |
| EP | 1 464 953 A1 | 10/2004 |
| EP | 1 947 452 A1 | 7/2008 |

OTHER PUBLICATIONS

English language translation of DE 102 26 945 A1.
Chun-Hao Chen et al: "A Wireless Bio-MEMS Sensor for C-Reactive Protein Detection Based on Nanomechanics", IEEE Transactions on Biomedical Engineering, IEEE Service Center, Piscataway, NJ, USA, vol. 56, No. 2, issued Feb. 1, 2009.
European Search Report mailed on Sep. 4, 2012.

* cited by examiner

*Primary Examiner* — Luan Van
*Assistant Examiner* — Gurpreet Kaur
(74) *Attorney, Agent, or Firm* — Abraham Hershkovitz; Hershkovitz & Associates, PLLC (57) ABSTRACT

Embodiments of the present disclosure set forth a biosensor for detecting a target. One example sensor includes a first electrode. The first electrode includes a first electron conducting molecule and a first probe. The first probe includes a second electron conducting molecule. The first probe is configured to bind to the target of interest in solution. The first and second electron conducting molecules are different.

34 Claims, 12 Drawing Sheets

BIOSENSOR

BACKGROUND OF THE DISCLOSURE

A biosensor is an analytical device for detecting a target molecule such as a biomolecule. Most biosensors are optical biosensors. An optical biosensor may include a metal which can absorb light and generate electron waves on the metal surface. The electron waves may occur at a specific angle and a specific wavelength of incident light, and thus are highly dependent on the surface of the metal. When a biomolecule attaches on the metal, a measurable signal may be generated.

Some biosensors are electrochemical biosensors. An electrochemical biosensor usually uses a catalyst as a probe. However, the applications of such an electrochemical biosensor are limited because the signal is low. New biosensors with higher signal to noise ratio are needed for accurate detection of target molecules of interest.

SUMMARY

Some embodiments of the present disclosure may generally relate to sensors for detecting a target. One example sensor may include an electrode treated with a first electron conducting molecule, and a probe conjugated with a second electron conducting molecule. The probe is attached to the first electrode and configured to bind to the target. The first and second electron conducting molecules may be different.

Some additional embodiments of the present disclosure may generally relate to methods for detecting a target. One example method may include contacting a sensor as describe above with a sample suspected of containing the target. When the target binds to the probe, a signal is generated. When the signal is detected, this indicates that the target is present in the sample.

Additional embodiments of the present disclosure may generally relate to a probe, such as an antibody, conjugated to an electron conducting molecule. Such an antibody molecule may be used in a sensor as described herein An example antibody is conjugated to a pyridine compound, a polyacetylene polymer, an azole compound, a polyaniline polymer or a derivative thereof. An electrode containing a probe conjugated to an electron conducting molecule, for example, an antibody conjugated to a pyridine compound, a polyacetylene polymer, an azole compound, a polyaniline polymer or a derivative thereof, is also provided.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

In this disclosure, the term "electron conducting molecule" generally refers to a compound that conducts electrons. The electron conducting molecule may provide a region of overlapping p-orbitals, which allow a delocalization of Tr electrons across adjacent aligned p-orbitals. The conductance of an electron conducting molecule may be examined with conductive atomic force microscopy. In some embodiments, the conductance of an electron conducting molecule useful in a chip for a biosensor as described herein is about 1 $\mu\Omega^{-1}$ to about 10 $\mu\Omega^{-1}$ at a about 0.01 volts voltage applied.

The term "probe" generally refers to a compound capable of binding to a target of interest (e.g., a biomolecule). For example, binding of a probe to a target may be with an affinity of about 100 piconewtons to about 500 piconewtons, Non-limiting examples of probes include antibodies, antibody fragments that retain the ability to bind to the target of interest, nucleic acids (e.g., DNA, RNA, aptamers), aptamers, antigens, and enzymes.

The term "target" generally refers to any molecule that is detectable with a biosensor as described herein. A target may include, but is not limited to, a biomolecule. Examples of targets that are detectable in the biosensors described herein include, but are not limited to, biomolecules (for example, virus, proteins, nucleic acids, and carbohydrates), and other types of small molecules such as lipid, hapten, and toxin.

Probes herein may contain an electron conducting molecule. The electronic transfer behavior of the probe may be induced with the overlapping p-orbitals provided by the electron conducting molecule. As a result, when a target binds to the probe, an electrical field change associated with the binding of the target and the probe may be amplified.

In some embodiments, a sensor for detecting a biomolecule includes a first electrode, a first probe, and first and second electron conducting molecules. The first probe recognizes and binds to a target of interest in a sample. In some embodiments, the first and second electron conducting molecules are different. The first electrode is treated with the first electron conducting molecule. The first electron conducting molecule may form a first chemical bond with the first electrode. The first chemical bond may be a covalent bond. In some embodiments, the first probe may form a chemical bond with the first electrode, for example, a covalent bond.

In some embodiments, the first probe is treated with a second electron conducting molecule. In some embodiments, the second electron conducting molecule is conjugated to the first probe, for example, covalently bound to the first probe directly or through a linker molecule. In some embodiments, the first probe may form a second chemical bond with the first electron conducting molecule. Therefore, the first probe may be attached to the first electrode through the first chemical bond and the second chemical bond, and may also contain an attached second electron conducting molecule.

The first probe may form a "lock and key" relationship with the target to be detected by the sensor. For example, the first probe may be DNA, RNA, a protein, an antibody, an antibody fragment, an aptamer, an antigen, or an enzyme. In some embodiments, the first probe is an antibody and the target is an antigen to which the antibody binds. When a first sample potentially including the target is introduced into the sensor and then flows over the first electrode, a first electrical field associated with the first electrode changes in response to the target binding to the first probe. A first signal is obtained based on the changed first electrical field. The sensor may contain a processor configured to detect the first signal. In some embodiments, detection of the first signal indicates that the first sample contains the target. By treating the first probe with the second electron conducing molecule, for example, attaching the second electron conducting molecule to the first probe, the conductivity of the first probe is increased. Therefore, when the target binds to the probe, the electrical field change associated with the binding is more readily detected. In certain embodiments, the sensor contains a first flow channel which is in contact with the first electrode and through which a first sample suspected of containing the target flows, and in which a signal is generated when the target binds to the first probe.

In some embodiments, the sensor includes a second electrode which contains a third electron conducting molecule and a second probe. The second probe is configured not to couple with the target to be detected by the sensor. In some embodiments, the binding affinity of the second probe for the target is less than about 50 piconewtons. The second electron conducting molecule may be the same or different than the first or second electron conducting molecule. In one embodiment, the third electron conducting molecule is the same as the first electron conducting molecule.

In some embodiments, the third electron conducting molecule forms a third chemical bond with the first electrode. The chemical bond may be a covalent bond. In some embodiments, the second probe may form a chemical bond with the first electrode. The chemical bond may be a covalent bond.

In some embodiments, the second probe contains a fourth electron conducting molecule, which may be the same or different than the first or second electron conducting molecule, and which may be the same or different than the third electron conducting molecule. In one embodiment, the third electron conducting molecule is attached, e.g., covalently attached, to the second electrode through the third chemical bond, the second probe is attached, e.g., covalently attached, to the third recognition molecule through a fourth chemical bond. The fourth electron conducting molecule may attached, e.g., covalently attached, to the second probe. For example, the second probe may be attached to the first electrode through the third chemical bond and the fourth chemical bond, and may also contain an attached fourth electron conducting molecule.

The second probe may form a "lock and key" relationship with a different biomolecule than the target to be detected by the sensor. In some nonlimiting embodiments, the second probe may be DNA, RNA, a protein, an antibody, an antibody fragment, an aptamer, an antigen, or an enzyme. In some embodiments, the second probe is an antibody that recognizes an antigen other than the target to be detected.

In some embodiments, the sensor contains a first flow channel in contact with the first electrode and a second flow channel in contact with the second electrode. The sensor may be configured such that a first sample suspected of containing the target of interest concurrently flows through the first flow channel and the second flow channel, or alternatively may be configured such that the first sample flows through the first and second flow channels non-concurrently. A first signal is generated in the first flow channel as described above. A second electrical field associated with the second electrode changes in response to the first sample. A second signal is obtained based on the changed second electrical field. The first signal and the second signal may be recorded for further processing.

In some embodiments, a second sample substantially free of the target of interest is introduced into the sensor through the first electrode and the second electrode, respectively. A third signal is generated in the first flow channel in response to the second sample flows through the first electrode. A fourth signal is generated in the second flow channel in response to the second sample flows through the second electrode. Based on the ratio of a first difference between the first signal and the third signal and a second difference between the second signal and the fourth signal, the sensor determines whether the target is present in the first sample.

In some embodiments, a biosensor is provided that contains at least two electrodes, wherein one electrode contains at least one probe and one electron conducting molecule, and another electrode contains at least one probe and two electron conducting molecules.

In one embodiment, a biosensor is provided that contains: (a) a first electrode containing a first probe as described herein and a first electron conducting molecule as described herein, wherein the first probe is configured to bind to a target of interest in a sample; and (b) a second electrode containing a second electron conducting molecule and a second probe that contains a third electron conducting molecule, wherein the probe does not bind to the target of interest, and wherein the first electron conducting molecule is the same or different than the second or third electron conducting molecule. Such a biosensor may be used in a method for detection of a target molecule of interest, as described herein.

In some embodiments, the first, second, third, and/or optional fourth electron conducting molecules may be an aromatic compound, a pyridine compound, a polyacetylene polymer, a thiophene compound, an azole compound, a polyaniline polymer or one of their derivatives. Some example electron conducting molecules include, but are not limited to, 3-(thiophen-2-yl)propanal, 3-phenylpropanal, 3-(1-pyrrol-2-yl)propanal, 3-(pyridin-2-yl)propanal, (E)-4-phenylbut-3-enal, (E)-4-(4-(E)-styrylphenyl)but-3-enal, (E)-4-(pyridin-2-yl)but-3-enal, (E)-4-(5-((E)-2-(pyridin-2-yl)vinyl)pyridine-2-yl)but-3-enal, (E)-hepta-4,6-dienal, (Z)-hepta-4,6-dienal, (E)-4-(cyclohex-2-enylidene)butanal, 2-(naphthalen-2-yl)acetaldehyde, 5"-formal-5-carboxyl-2,2',5',2"-trithiophene, p-4'-formal-4-carboxyl-1,1'-bibenzene, 5'-(methyl)thiol-5-formal-2,2'-bithiolphene, and one of their derivatives.

In some embodiments, a method for detecting a target is disclosed. The method includes contacting any of the sensors described above with a first sample suspected of containing the target, and detecting a first signal as described above when the target binds to the first probe. In some embodiments, detection of the first signal indicates that the target is present in the first sample. Optionally, a second signal, a third signal, and a fourth signal are detected as described above and the first, second, third, and fourth signals are processed to determine whether the target is present in the first sample.

In some embodiments, the method includes treating a first electrode with a first electron conducting molecule, conjugating a first probe with a second electron conducting molecule, and attaching the first probe on the first electrode. The first probe is configured to bind to the target.

The method may further include treating a second electrode with the same first electron conducting molecule and attaching a second probe on the second electrode. The second probe is configured not to bind to the target.

The method may further include introducing a first sample potentially including the target to flow through the first electrode and the second electrode concurrently to obtain a first signal and a second signal, respectively. The method may further include introducing a second sample substantially free of the target to flow through the first electrode and the second electrode concurrently to obtain a third signal and a fourth signal. The method may further include determining whether the first sample includes the target based on quantitation of the first signal, second, third, and fourth signals, as described above.

Figure 1:
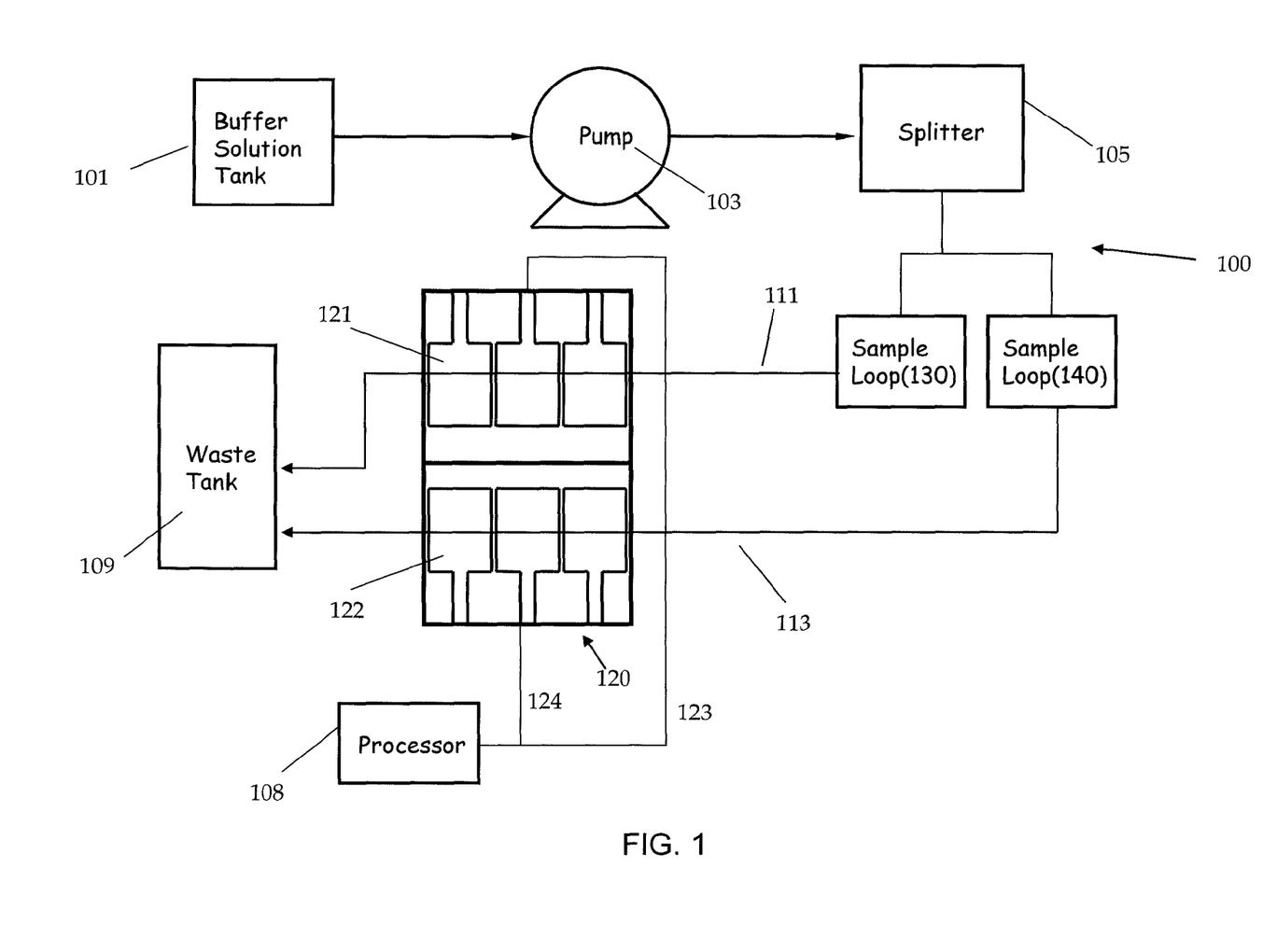
FIG. 1 shows an illustrative embodiment of a sensor for detecting a biomolecule.

FIG. 1 is an illustrative embodiment of a sensor 100 for detecting a target of interest. The sensor 100 includes a buffer solution tank 101, a pump 103, a splitter 105, a first sample loop 130, a second sample loop 140, a biochip 120, a waste tank 109, and a processor 108. The first sample loop 130 and the second sample loop 140 are configured to store a sample potentially including a target to be detected by the sensor. After the sensor is activated, the pump 103 pumps a buffer solution stored in the buffer solution tank 101 to flush the first sample loop 130 and the second sample loop 140. The sample is then mixed with the buffer solution and flows through the biochip 120 from a first channel 111 and a second channel 113. The biochip 120 includes a first electrode set 121 and a second electrode set 122. The sample eventually is collected in a waste tank 109 after the sample flows through the biochip 120.

A first probe may be attached on the first electrode set 121 and the first probe is configured to bind to the target to be detected by the sensor 100. A second probe may be attached on the second electrode set 122 and the second probe is configured not to bind to the target to be detected by the sensor 100.

When the sample flows through the first electrode set 121 and the second electrode set 122, the electrical fields of the first electrode set 121 and the second electrode set 122 may change, respectively. The signals reflecting the electrical field changes of the first electrode set 121 and the second electrode set 122 may then be sent to the processor 108 through wires 123 and 124 for further processing. The processor 108 is configured to determine whether the target to be detected by the sensor exists in the sample.

Figure 2:
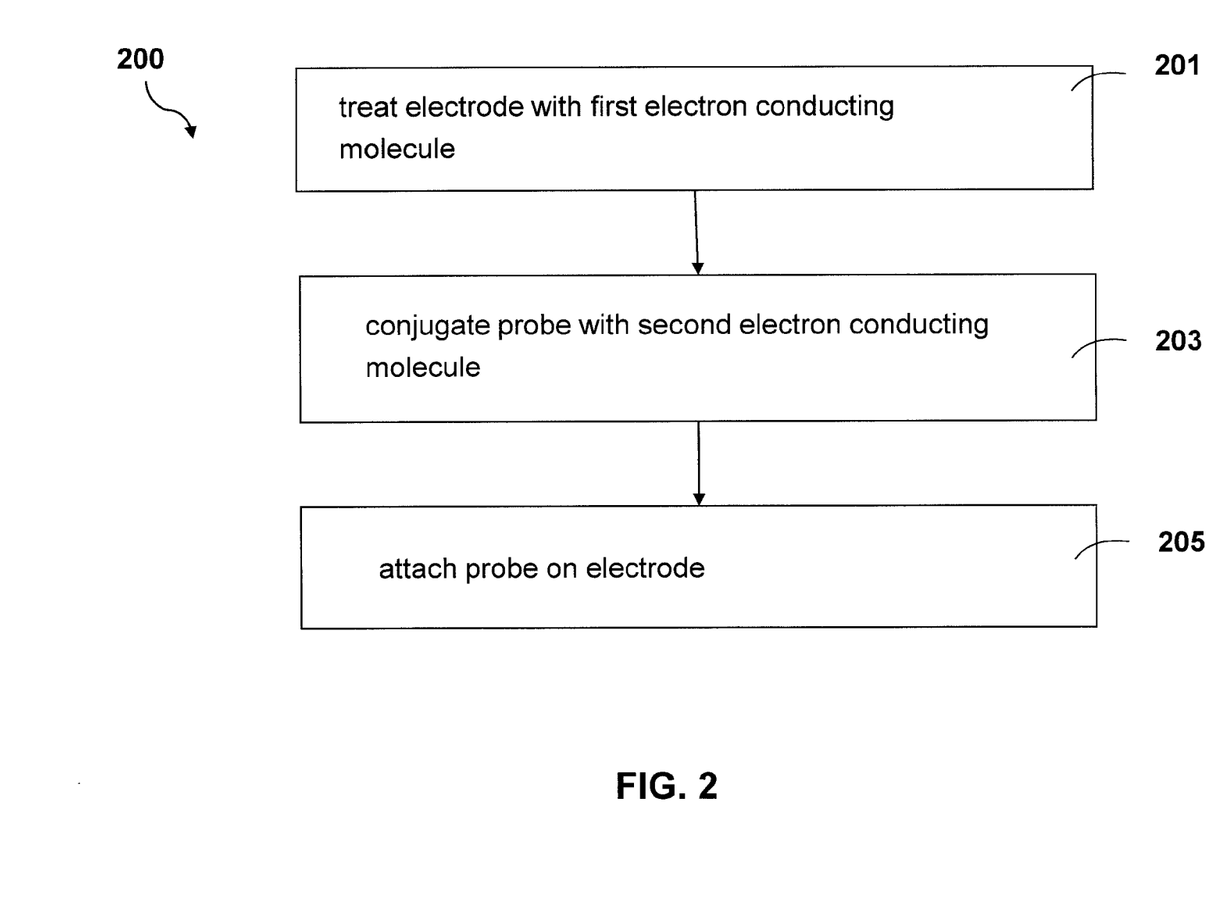
FIG. 2 shows a flow chart of an illustrative embodiment of a method for detecting a biomolecule.

FIG. 2 shows a flow chart of an illustrative embodiment of a method 200 for detecting a biomolecule. The method 200 includes steps 201, 203, and 205. In step 201, an electrode is treated with a first electron conducting molecule. The first electron conducting molecule may form a covalent bond with the electrode. The electrode may be metal, for example gold, platinum, copper . . . etc. Some example first electron conducting molecule include, but not limited to, 3-(thiophen-2-yl)propanal, 3-phenylpropanal, 3-(1-pyrrol-2-yl)propanal, 3-(pyridin-2-yl)propanal, (E)-4-phenylbut-3-enal, (E)-4-(4-(E)-styrylphenyl)but-3-enal, (E)-4-(pyridin-2-yl)but-3-enal, (E)-4-(5-((E)-2-(pyridin-2-yl)vinyl)pyridin-2-yl)but-3-enal, (E)-hepta-4,6-dienal, (Z)-hepta-4,6-dienal, (E)-4-(cyclohex-2-enylidene)butanal, 2-(naphthalen-2-yl)acetaldehyde, 5''-formal-5-carboxyl-2,2',5',2''-trithiophene, p-4'-formal-4-carboxyl-1,1'-bibenzene, 5'-(methyl)thiol-5-formal-2,2'-bithiolphene, and one of their derivatives.

In step 203, a probe is conjugated with a second electron conducting molecule. The probe may be DNA, RNA, protein, antibody, antigen, or enzyme. The second electron conducting molecule may be different than the first electron conducting molecule. Some example second electron conducting molecule include, but not limited to, 3-(thiophen-2-yl)propanal, 3-phenylpropanal, 3-(1-pyrrol-2-yl)propanal, 3-(pyridin-2-yl)propanal, (E)-4-phenylbut-3-enal, (E)-4-(4-(E)-styrylphenyl)but-3-enal, (E)-4-(pyridin-2-yl)but-3-enal, (E)-4-(5-((E)-2-(pyridin-2-yl)vinyl)pyridin-2-yl)but-3-enal, (E)-hepta-4,6-dienal, (Z)-hepta-4,6-dienal, (E)-4-(cyclohex-2-enylidene)butanal, 2-(naphthalen-2-yl)acetaldehyde, 5''-formal-5-carboxyl-2,2',5',2''-trithiophene, p-4'-formal-4-carboxyl-1,1'-bibenzene, 5'-(methyl)thiol-5-formal-2,2'-bithiolphene, and one of their derivatives.

In step 205, the probe is attached on the electrode. The probe may form a covalent bond with the first electron conducting molecule. Through the covalent bond between the probe and the first electron conducting molecule, and the covalent bond between the first electron conducting molecule and the electrode, the probe is attached on the electrode.

Figure 3A:
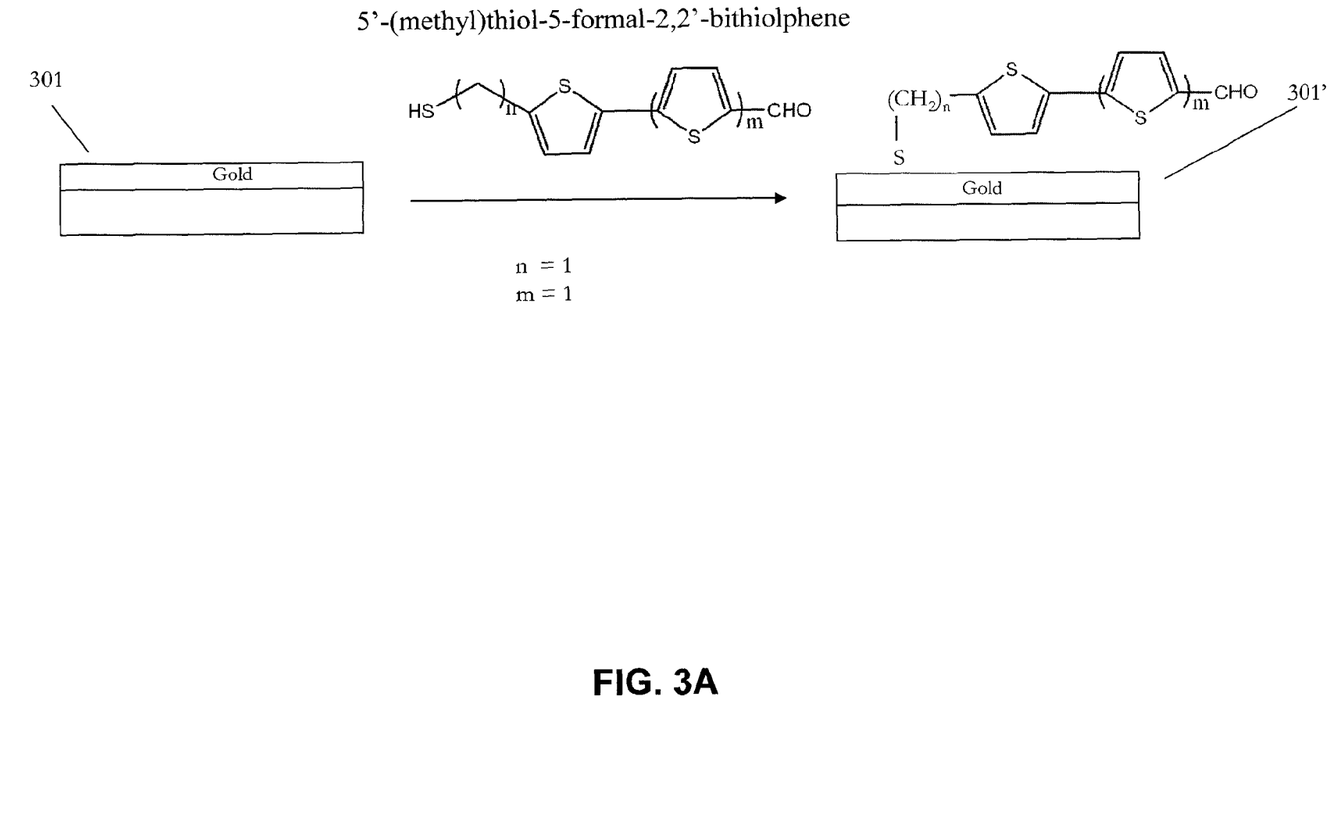
FIGS. 3A-3F shows an illustrative embodiment of a method for preparing two electrodes in a sensor for detecting a biomolecule.

FIGS. 3A-3F shows an illustrative embodiment of a method for preparing two electrodes in a sensor for detecting a biomolecule. In FIG. 3A, a first gold electrode 301 is treated with 5'-(methyl)thiol-5-formal-2,2'-bithiolphene. 5'-(methyl)thiol-5-formal-2,2'-bithiolphene is used as an electron conducting molecule and forms a first covalent bond with the treated first gold electrode 301'. The electron conductivity of the treated first gold electrode 301' is then promoted. In some embodiments, the treated first gold electrode 301' is arranged in a first channel of the sensor.

Figure 3B:
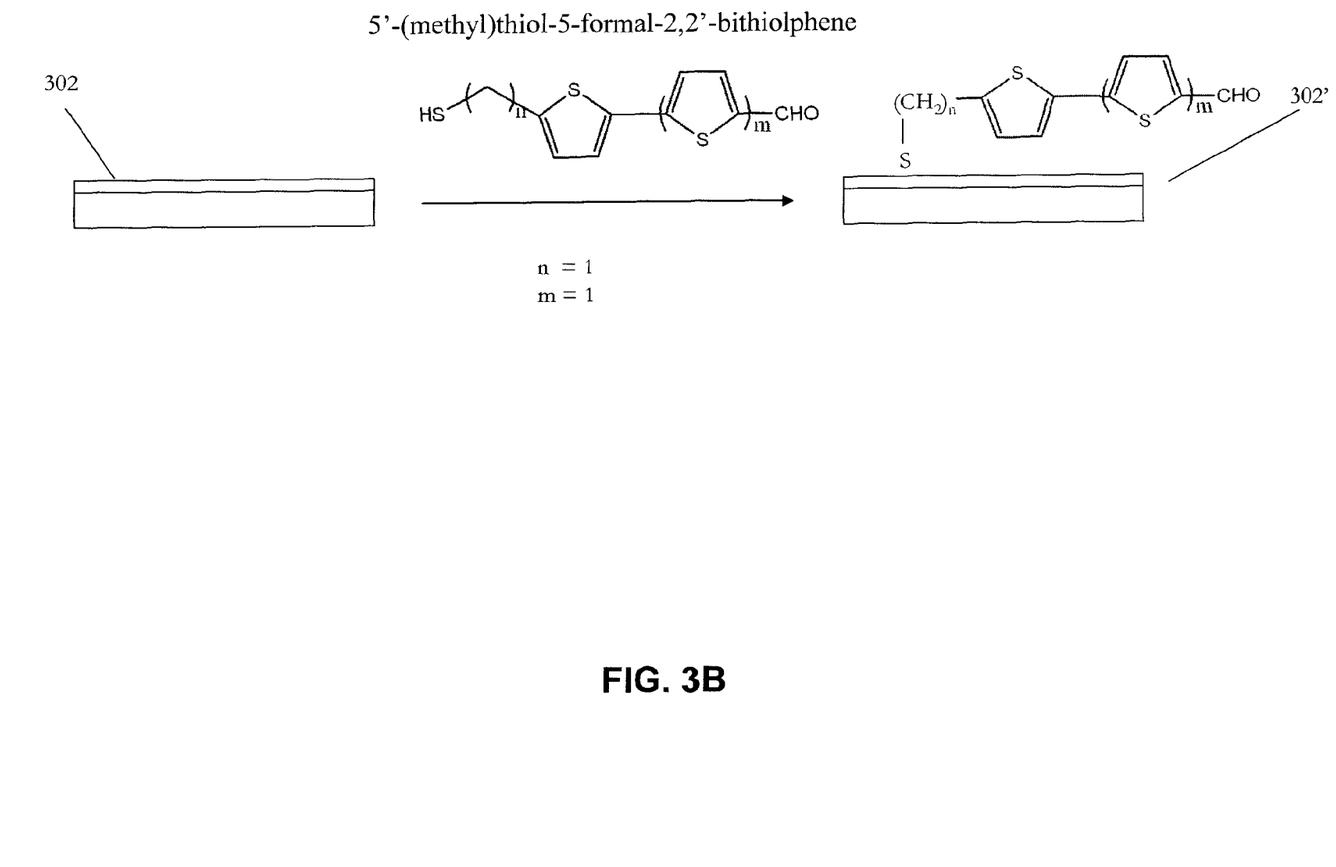

In FIG. 3B, a second gold electrode 302 is treated with 5'-(methyl)thiol-5-formal-2,2'-bithiolphene. 5'-(methyl)thiol-5-formal-2,2'-bithiolphene is used as an electron conducting molecule and forms a second covalent bond with the treated second gold electrode 302'. The electron conductivity of the treated second gold electrode 302' is then promoted. In some embodiments, the treated second gold electrode 302' is arranged in a second channel of the sensor.

Figure 3C:
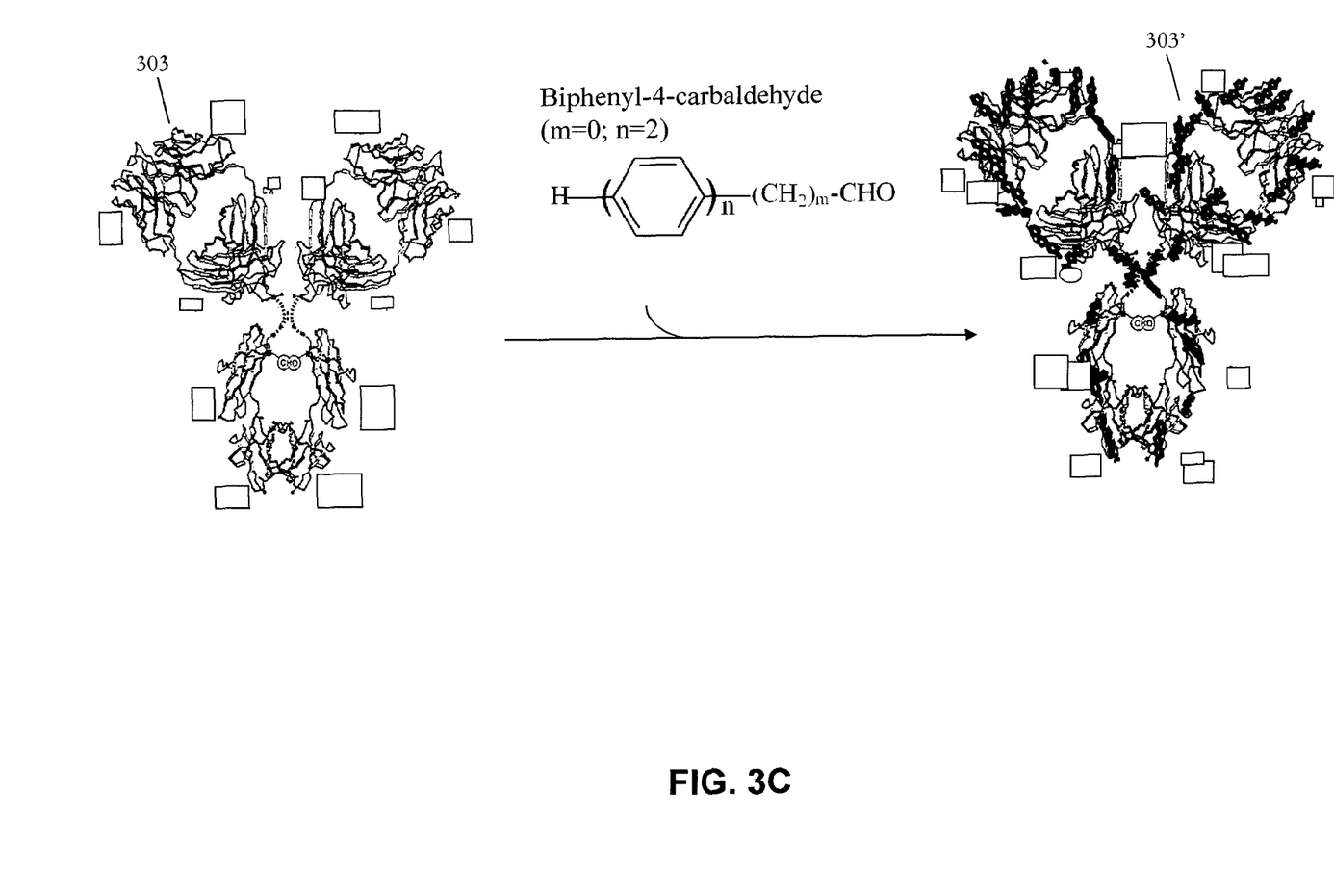

In FIG. 3C, an anti-(HPV HR) antibody 303 is treated with biphenyl-4-carbaldehyde so that biphenyl-4-carbaldehyde conjugates to the treated anti-(HPV HR) antibody 303'. Biphenyl-4-carbaldehyde is used as an electron conducting molecule. The electron conductivity of the treated anti-(HPV HR) antibody 303' is promoted.

Figure 3D:
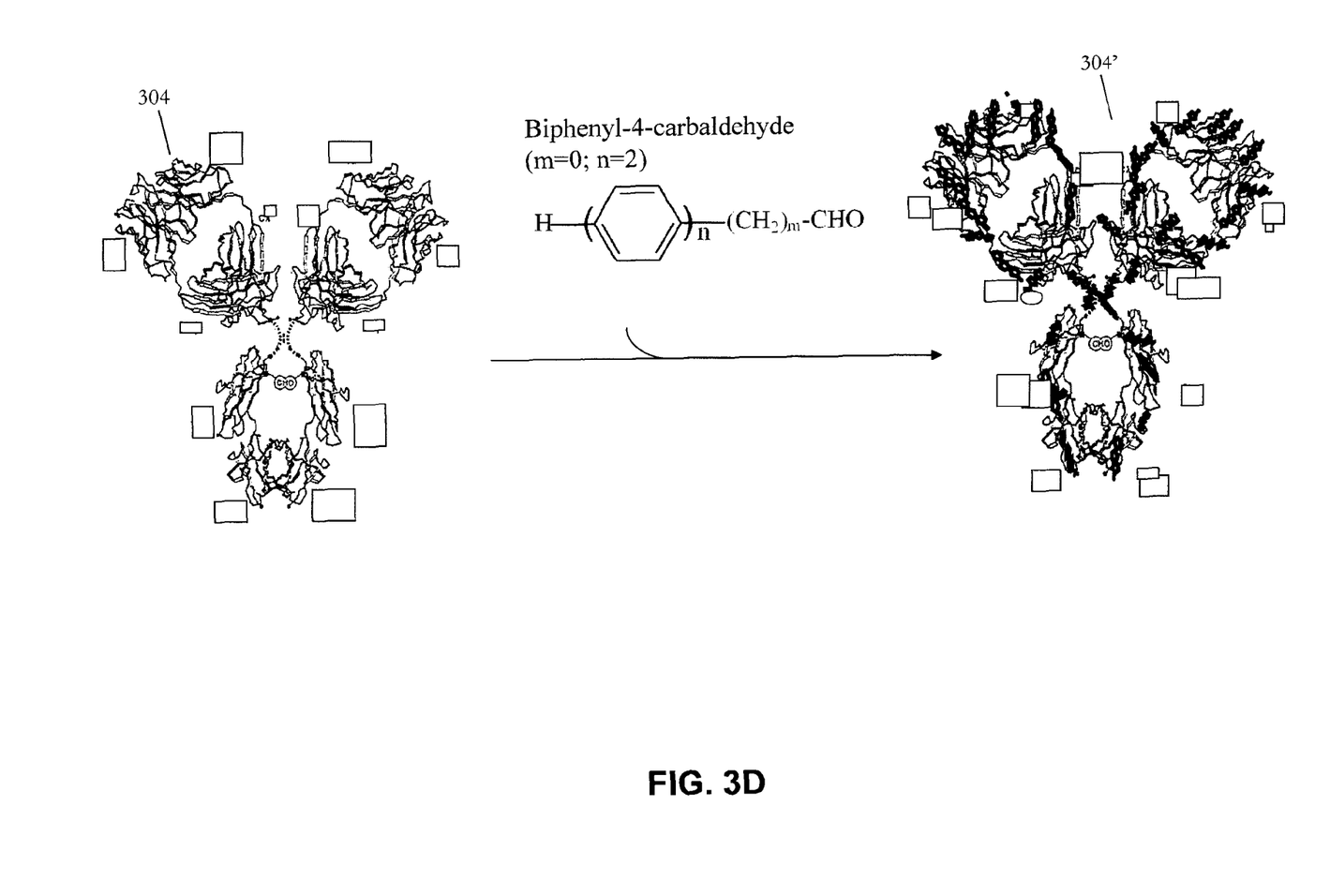

In FIG. 3D, an anti-caffeine antibody 304 is treated with biphenyl-4-carbaldehyde so that biphenyl-4-carbaldehyde conjugates to the treated anti-caffeine antibody 304'. Biphenyl-4-carbaldehyde is used as an electron conducting molecule. The electron conductivity of the treated anti-caffeine antibody 304' is promoted.

Figure 3E:
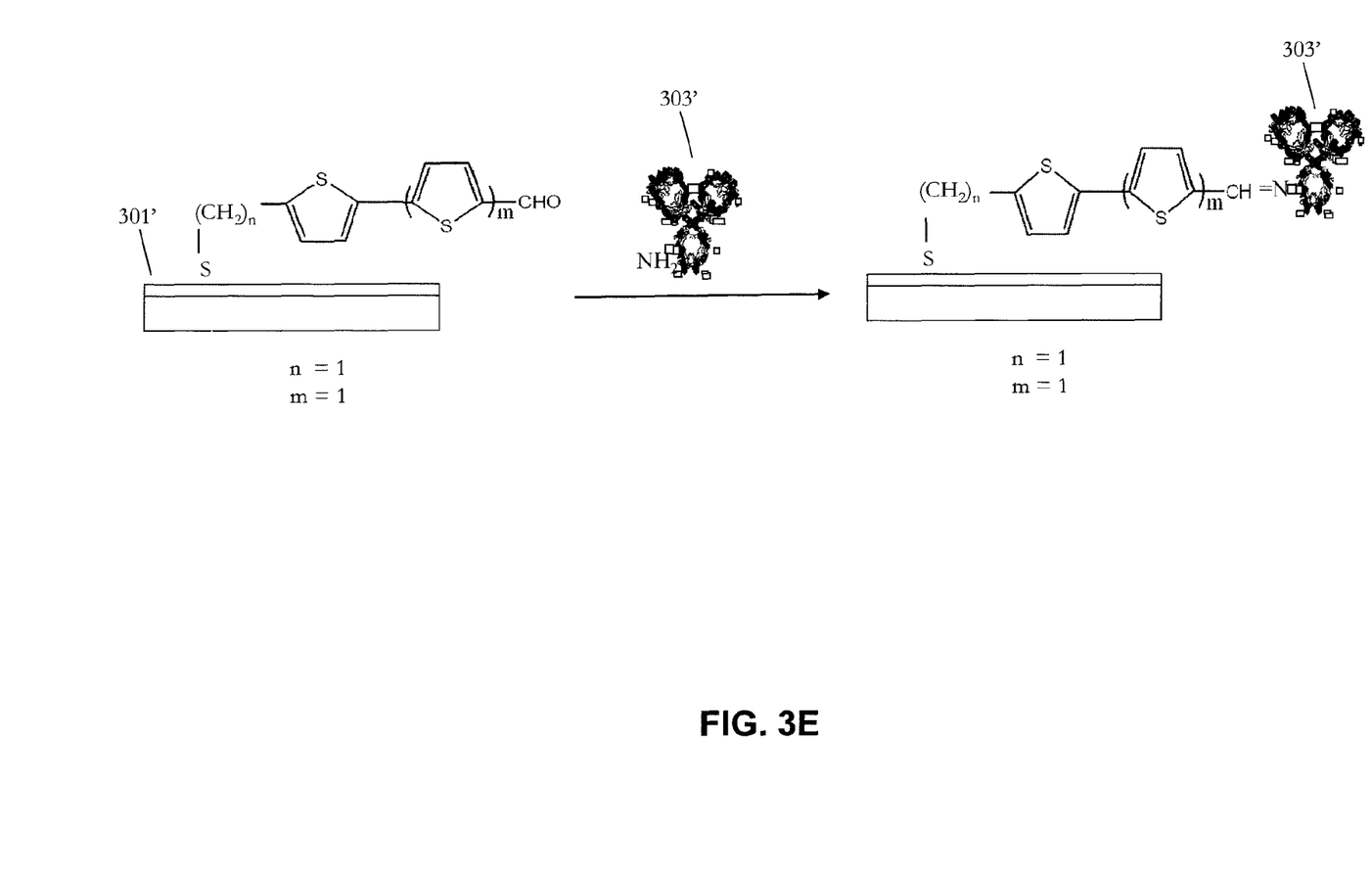

In FIG. 3E, the treated anti-(HPV HR) antibody 303' is attached on the treated first gold electrode 301'. In some embodiments, an amine group of the treated anti-(HPV HR) antibody 303' may form a third covalent bond with 5'-(methyl)thiol-5-formal-2,2'-bithiolphene. Through the first and the third covalent bonds, the treated anti-(HPV HR) antibody 303' is attached on the treated first gold electrode 301'.

Figure 3F:
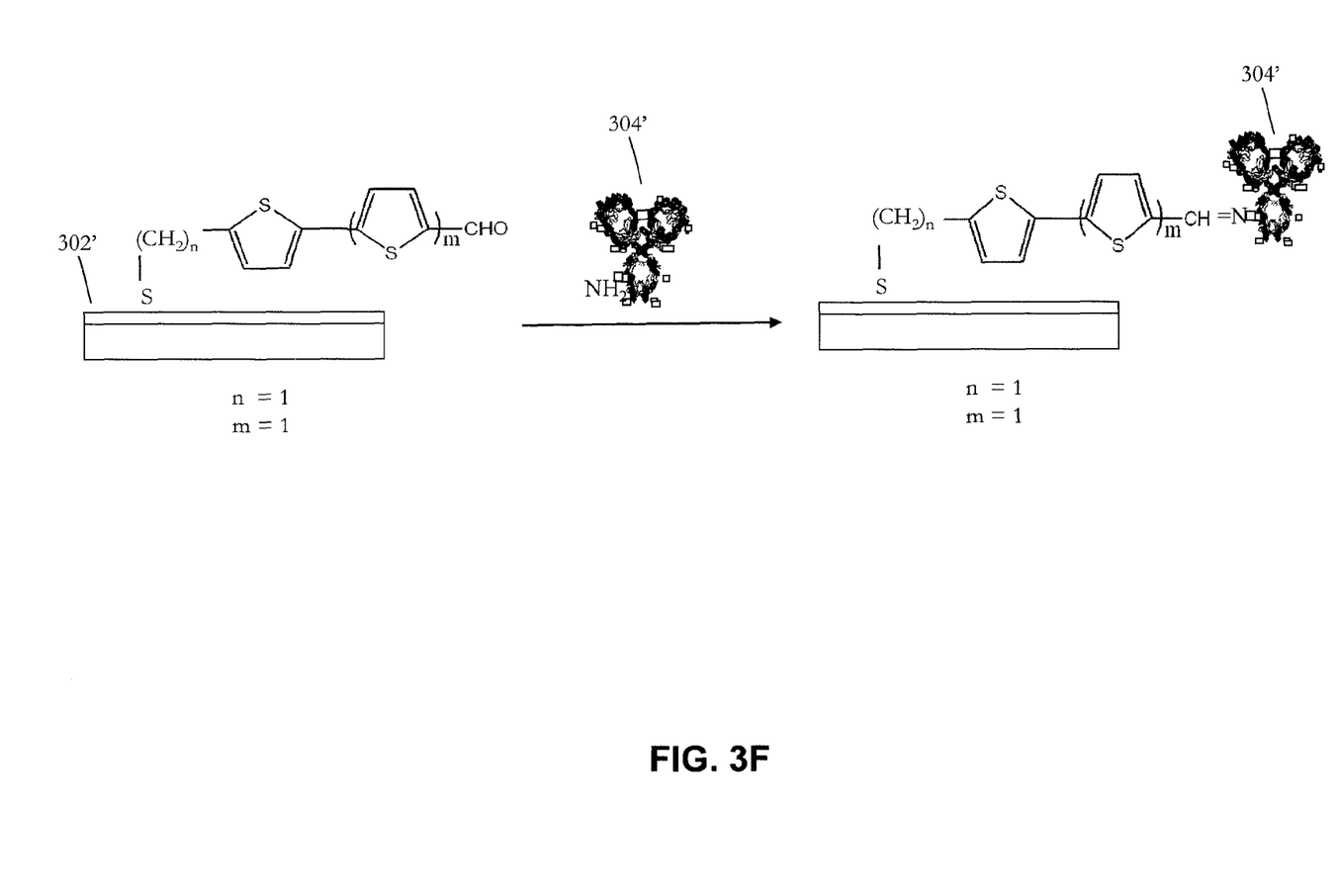

In FIG. 3F, the treated anti-caffeine antibody 304' is attached on the treated second gold electrode 302'. In some embodiments, an amine group of the treated anti-caffeine antibody 304' may form a fourth covalent bond with 5'-(methyl)thiol-5-formal-2,2'-bithiolphene. Through the second and the fourth covalent bonds, the treated anti-caffeine antibody 304' is attached on the treated second gold electrode 302'.

Example 1

A bare sensor chip including two gold electrode set was mounted in Vsensor® V11A3 sensor (Vsense Biotech.Ltd, Taipei, Taiwan). In the sensor, a first flow channel crossed the first gold electrode set and a second flow channel crossed the second gold electrode set. After the sensor was activated, a pump drained phosphate buffered saline (PBS) buffer from a buffer solution tank. PBS buffer has a pH value of 7.2 and flowed over the sensor chip at a rate of 20 μl/min. Then an electron conducing molecule, 10 mM 5'-(methyl)thiol-5-formal-2,2'-bithiolphene solution was injected to the sensor and flushed with PBS buffer. 5'-(methyl)thiol-5-formal-2,2'-bithiolphene solution and PBS buffer then flowed over the first gold electrode set and the second gold electrode set for 5 minutes. Finally, the first gold electrode set and the second gold electrode set were rinsed with PBS buffer for another 15 minutes.

A 200 mg/ml monoclonal anti-(HPV HR) antibody (Abcam, ab75574, Cambridge, UK) solution was formed in PBS buffer. A 10 mM Biphenyl-4-carbalsehyde, another electron conducting molecule, (MerckSchuchardt OHG, 8.41238.0010, Hohenbrunn, Germany) solution in 50% ethanol/50% water was added to the antibody solution. After well mixed, a conjugated monoclonal anti-(HPV HR) antibody solution was formed.

A 200 μg/ml monoclonal anti-caffeine antibody (Abcam, ab15221, Cambridge, UK) solution was formed in PBS buffer. A 10 mM Biphenyl-4-carbalsehyde, another electron conducting molecule, (MerckSchuchardt OHG, 8.41238.0010, Hohenbrunn, Germany) solution in 50% ethanol/50% water was added to the antibody solution. After well mixed, a conjugated monoclonal anti-caffeine antibody solution was formed.

The conjugated monoclonal anti-(HPV HR) antibody solution was then injected to the sensor through a first sample loop and then flowed over the first gold electrode set. Then the first gold electrode set was flushed with PBS buffer. The flow rate of PBS buffer was 20 μl/min for 10 minutes. The first gold electrode set was then rinsed again with PBS buffer for another 10 minutes, where the flow rate of PBS buffer was kept at 20 μl/min.

The conjugated monoclonal anti-caffeine antibody solution was injected to the sensor through a second sample loop and then flowed over the second gold electrode set. Then the second gold electrode set was flushed with PBS buffer. The flow rate of PBS buffer was 20 μl/min for 10 minutes. The second gold electrode set was then rinsed again with PBS buffer for another 10 minutes, where the flow rate of PBS buffer was kept at 20 μl/min.

A Human Papillomavirus 16 (HPV16) infected patient sample was diluted to 0.1%, 1%, 2%, 5%, and 10%. The diluted samples were injected to the sensor in sequence. Each diluted sample flowed through the first gold electrode set and the second gold electrode set concurrently.

We used the same chip repeatedly to study each diluted concentration of the patient sample. This was accomplished by washing away the associated HPV16 with acidic glycine buffer (0.1 M, pH 2.5).

A sample from a healthy person was used as a control group. The control sample was also diluted to 0.1%, 1%, 2%, 5%, and 10%. The diluted control samples were injected to the sensor in sequence. Each diluted control sample flowed through the first gold electrode set and the second gold electrode set concurrently. We also used acidic glycine buffer to flush the chip between two injections.

Figure 4A:
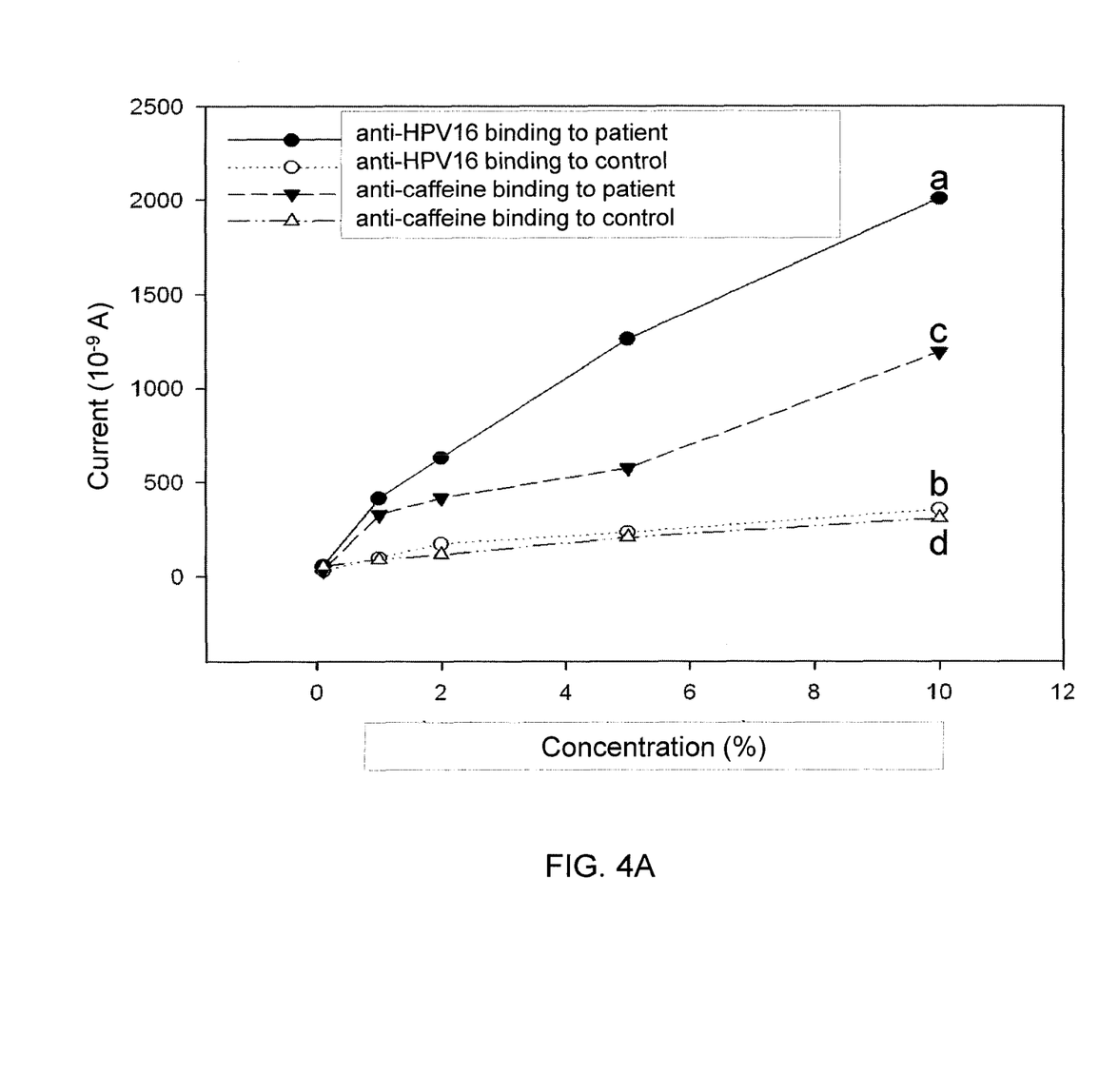
FIG. 4A shows a chart of an illustrative embodiment illustrating currents detected at various concentrations diluted from a Human Papillomavirus 16 (HPV16) infected patient sample and a control sample.

The currents detected by the sensor in response to each injection were showed in FIG. 4A. In FIG. 4A, relatively high currents were detected for the HPV16 infected patient samples when the patient sample concentration was 1%, 2%, 5%, and 10%, respectively. The ratio of the current value of (point a-point b)/(point c-point d) was used to determine whether HPV16 antigen presents in the diluted samples.

Figure 4B:
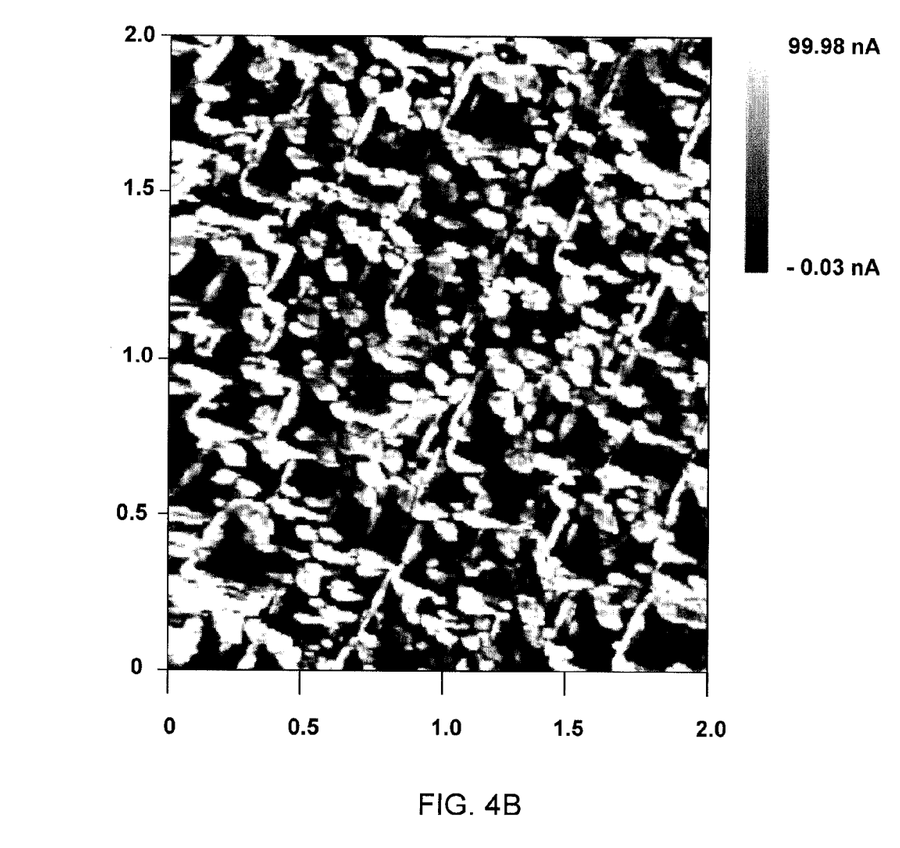
FIG. 4B shows a conductive image of an electrode including a monoclonal anti-(HPV HR) antibody conjugated with biphenyl-4-carbalsehyde scanned by conductive atomic force microscopy at a biased voltage (about 0.01 volts) applied.

FIG. 4B shows a conductive image of an electrode including a monoclonal anti-(HPV HR) antibody conjugated with biphenyl-4-carbalsehyde scanned by conductive atomic force microscopy at a biased voltage (about 0.01 volts) applied. The image shows the conductance profile on a surface of the electrode. The unit of X-axis is μm and the unit of Y-axis is μm. The brighter parts indicate relatively high conductance (e.g., about 99.98 nano-Ampere). The darker parts indicate relatively low conductance (e.g., 0 nano-Ampere).

Example 2

A bare sensor chip including two gold electrode set was mounted in Vsensor® V11A3 sensor (Vsense Biotech.Ltd, Taipei, Taiwan). In the sensor, a first flow channel crossed the first gold electrode set and a second flow channel crossed the second gold electrode set. After the sensor was activated, a pump drained phosphate buffered saline (PBS) buffer from a buffer solution tank. PBS buffer has a pH value of 7.2 and flowed over the sensor chip at a rate of 20 μl/min. Then an electron conducing molecule, 10 mM 5'-(methyl)thiol-5-formal-2,2'-bithiolphene solution was injected to the sensor through a sample loop and flushed with PBS buffer. 5'-(methyl)thiol-5-formal-2,2'-bithiolphene solution and PBS buffer then flowed over the first gold electrode set and the second gold electrode set for 5 minutes. Finally, the first gold electrode set and the second gold electrode set were rinsed with PBS buffer for another 15 minutes.

A 200 μg/ml monoclonal anti-(EV71) antibody (Millipore, 3321, Billerica, Mass., USA) solution was formed in PBS buffer. A 10 mM Biphenyl-4-carbalsehyde, another electron conducting molecule, (MerckSchuchardt OHG, 8.41238.0010, Hohenbrunn, Germany) solution in 50% ethanol/50% water was added to the antibody solution. After well mixed, a conjugated monoclonal anti-(EV71) antibody solution was formed.

A 200 μg/ml monoclonal anti-acrosomal protein (Abcam, ab4569, Cambridge, UK) solution was formed in PBS buffer. A 10 mM Biphenyl-4-carbalsehyde (MerckSchuchardt OHG, 8.41238.0010, Hohenbrunn, Germany) solution in 50% ethanol/50% water was added to the anti-acrosomal protein solution. After well mixed, a conjugated anti-acrosomal protein solution was formed.

The conjugated monoclonal anti-(EV71) antibody solution was then injected to the sensor through a first sample loop and then flowed over the first gold electrode set. Then the first gold electrode set was flushed with PBS buffer. The flow rate of PBS buffer was 20 μl/min for 10 minutes. The first gold electrode set was then rinsed again with PBS buffer for another 10 minutes, where the flow rate of PBS buffer was kept at 20 µl/min.

The conjugated anti-acrosomal protein solution was then injected to the sensor through a second sample loop and then flowed over the second gold electrode set. Then the second gold electrode set was flushed with PBS buffer. The flow rate of PBS buffer was 20 µl/min for 10 minutes. The second gold electrode set was then rinsed again with PBS buffer for another 10 minutes, where the flow rate of PBS buffer was kept at 20 µl/min.

An EV71 infected patient sample was diluted to 0.1%, 1%, 2%, 5%, and 10%. The diluted samples were injected to the sensor in sequence. Each diluted sample flowed through the first gold electrode set and the second gold electrode set concurrently.

We used the same chip repeatedly to study each diluted concentration of the patient sample. This was accomplished by washing away the associated EV71 with acidic glycine buffer (0.1 M, pH 2.5).

A sample from a healthy person was used as a control group. The control sample was also diluted to 0.1%, 1%, 2%, 5%, and 10%. The diluted control samples were injected to the sensor in sequence. Each diluted control sample flowed through the first gold electrode set and the second gold electrode set concurrently. We also used acidic glycine buffer to flush the chip between two injections.

Figure 4C:
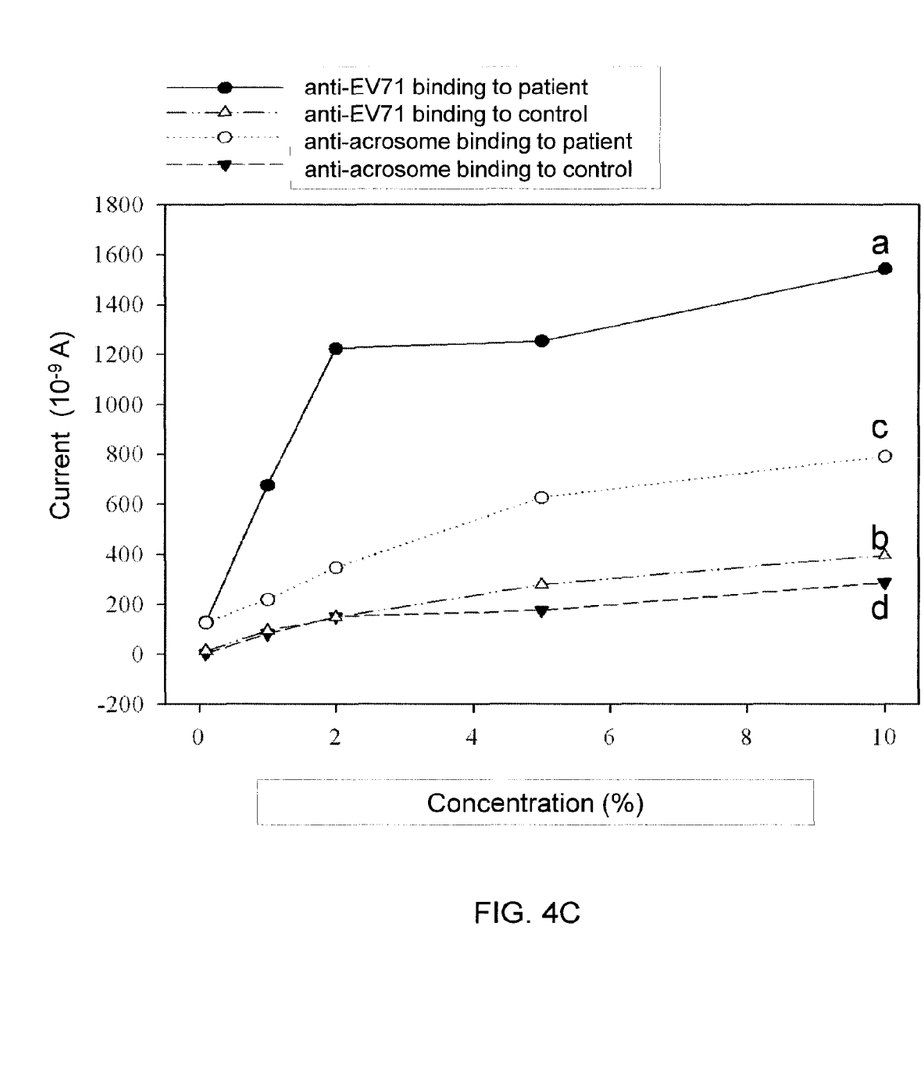
FIG. 4C shows a chart of an illustrative embodiment illustrating currents detected at various diluted concentrations from an Enterovirus 71 (EV71) infected patient sample and a control sample.

The currents detected by the sensor in response to each injection were showed in FIG. 4C. In FIG. 4C, relatively high currents were detected for the EV71 infected patient samples when the patient sample concentration was 0.1%, 1%, 2%, 5%, and 10%, respectively. The ratio of the current value of (point a–point b)/(point c–point d) was used to determine whether EV71 antigen presents in the diluted samples.

Example 3

A bare sensor chip including two gold electrode set was mounted in Vsensor® V11A3 sensor (Vsense Biotech.Ltd, Taipei, Taiwan). In the sensor, a first flow channel crossed the first gold electrode set and a second flow channel crossed the second gold electrode set. After the sensor was activated, a pump drained phosphate buffered saline (PBS) buffer from a buffer solution tank. PBS buffer has a pH value of 7.2 and flowed over the sensor chip at a rate of 50 µl/min. Then an electron conducing molecule, 10 mM p-4'-formal-4-carboxyl-1,1'-bibenzene (CHO—$(C_6H_4)_2$—COOH) solution was injected to the sensor through a sample loop and flushed with PBS buffer. p-4'-formal-4-carboxyl-1,1'-bibenzene solution and PBS buffer then flowed over the first gold electrode set and the second gold electrode set for 18 minutes. Finally, the first gold electrode set and the second gold electrode set were rinsed with PBS buffer for another 15 minutes. Then a mixture of 400 mM EDC and 100 mM NHS (volume of EDC/volume of NHS=1/1) was injected and flowed over the sensor chip at a flow rate of 20 µl/min for 15 min.

A 200 µg/ml monoclonal anti-(Lect2) antibody (Santa Cruz, sc-99036, Santa Cruz, Calif., USA) solution was formed in acetate buffer (pH is 4.8). A 10 mM Biphenyl-4-carbalsehyde, another electron conducting molecule, (MerckSchuchardt OHG, 8.41238.0010, Hohenbrunn, Germany) solution in 50% ethanol/50% water was added to the antibody solution. After well mixed, a conjugated monoclonal anti-(Lect2) antibody solution was formed.

A 200 µg/ml monoclonal anti-acrosomal protein (Abcam, ab4569, Cambridge, UK) solution was formed in PBS buffer. A 10 mM Biphenyl-4-carbalsehyde (MerckSchuchardt OHG, 8.41238.0010, Hohenbrunn, Germany) solution in 50% ethanol/50% water was added to the anti-acrosomal protein solution. After well mixed, a conjugated anti-acrosomal protein solution was formed.

The conjugated monoclonal anti-(Lect2) antibody solution was then injected to the sensor through a first sample loop and flowed over the first gold electrode set. Then the first gold electrode set was flushed with PBS buffer. The flow rate of PBS buffer was 20 µl/min for 10 minutes. The first gold electrode set was then rinsed again with PBS buffer for another 10 minutes, where the flow rate of PBS buffer was kept at 20 µl/min.

The conjugated anti-acrosomal protein solution was then injected to the sensor through a second sample loop and then flowed over the second gold electrode set. Then the second gold electrode set was flushed with PBS buffer. The flow rate of PBS buffer was 20 µl/min for 10 minutes. The second gold electrode set was then rinsed again with PBS buffer for another 10 minutes, where the flow rate of PBS buffer was kept at 20 µl/min.

A HCC (Hepatocellular carcinoma) patient sample containing Lect2 biomarker molecules was diluted to 0.1%, 1%, 2%, 5%, and 10%. The diluted samples were injected to the sensor in sequence. The flow channel switch controlled each diluted sample to flow through the first gold electrode set and the second gold electrode set concurrently.

We used the same chip repeatedly to study each diluted concentration of the patient sample. This was accomplished by washing away the associated Lect2 with acidic glycine buffer (0.1 M, pH 2.5).

A sample from a healthy person was used as a control group. The control sample was also diluted to 0.1%, 1%, 2%, 5%, and 10%. The diluted control samples were injected to the sensor in sequence. The flow channel switch controlled each diluted control sample to flow through the first gold electrode set and the second gold electrode set concurrently. We also used acidic glycine buffer to flush the chip between two injections.

Figure 4D:
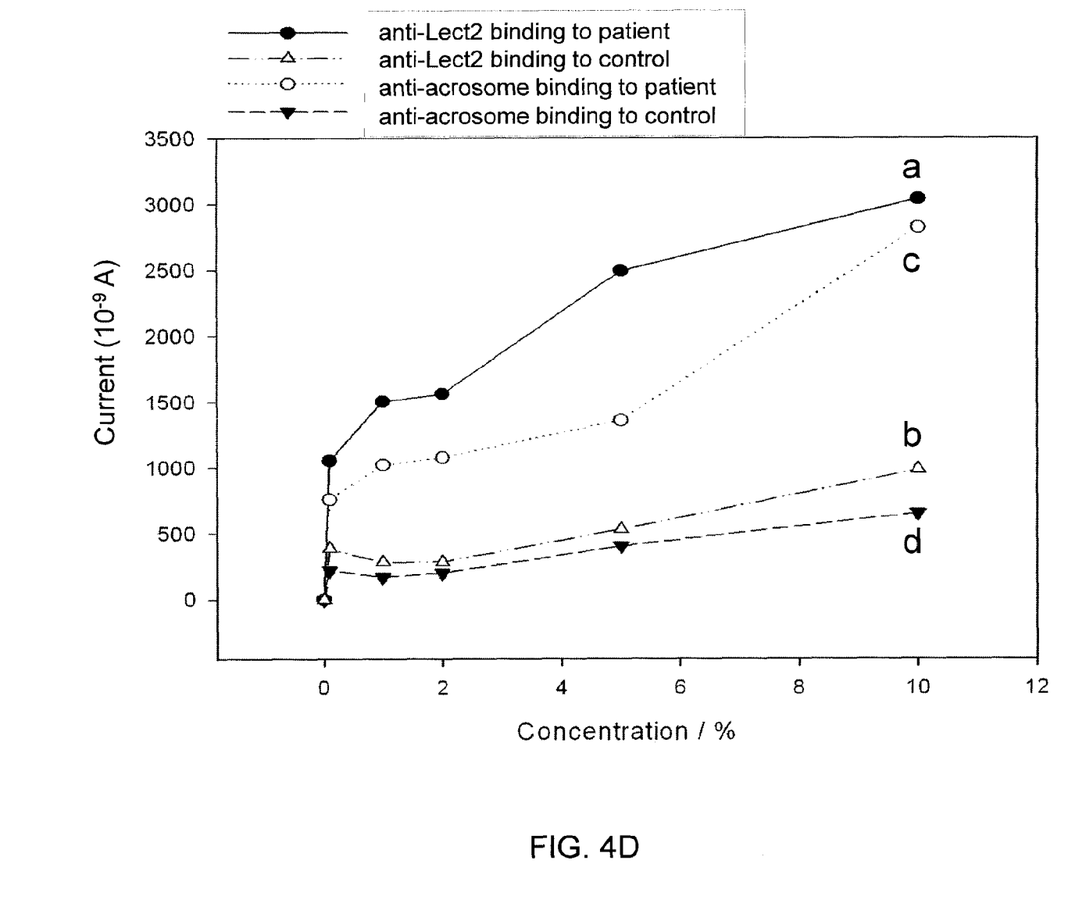
FIG. 4D shows a chart of an illustrative embodiment illustrating currents detected at various diluted concentrations from a Leukocyte cell-derived chemotaxin-2 infected patient sample and a control sample.

The currents detected by the sensor in response to each injection were showed in FIG. 4D. In FIG. 4D, relatively high currents were detected for the HCC (Hepatocellular carcinoma) patient samples containing Lect 2 biomarker molecules when the patient sample concentration was 0.1%, 1%, 2%, 5%, and 10%, respectively. The ratio of the current value of (point a–point b)/(point c–point d) was used to determine whether HPV16 antigen presents in the diluted samples.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:
1. A sensor for detecting a target of interest, comprising:
   a first electrode consisting of (i) a first electron conducting molecule; and (ii)
   a first probe comprising a second electron conducting molecule, wherein the first
   probe is configured to bind to the target of interest in solution, wherein the first and second electron conducting molecules are different, the first electron conducting molecule is covalently attached to the first electrode, the first probe is covalently attached to the first electron conducting molecule or the first electrode; and a second electrode consisting of a third electron conducting molecule and a second probe, wherein the second probe does not bind to the target of interest, and wherein the third electron conducting molecule is covalently attached to the second electrode or the second probe is covalently attached to the third electron conducting molecule and wherein the third electron conducting molecule is different than the first or second electron conducting molecule.

2. The sensor of claim 1, wherein the first probe is covalently attached to the first electrode.

3. The sensor of claim 1, wherein the first probe is covalently attached to the first electron conducting molecule.

4. The sensor of claim 1, wherein the second probe comprises a fourth electron conducting molecule, wherein the fourth electron conducting molecule is the same or different than the third electron conducting molecule.

5. The sensor of claim 4, wherein the fourth electron conducting molecule is the same as the third electron conducting molecule.

6. The sensor of claim 1, further comprising a first flow channel which is in contact with the first electrode and configured such that a sample comprising the target of interest flows through the first flow channel and generates a first signal when the target binds to the first probe, and further comprising a second flow channel which is in contact with the second electrode and configured such that the sample flows through the second flow channel and generates a second signal.

7. The sensor of claim 6, further comprising a processor configured to detect the first signal and the second signal.

8. The sensor of claim 7, wherein the target of interest is detected by comparing a value associated with the first and second signals to a predetermined value, wherein the value associated with the first and second signals being greater than the predetermined value indicates that the target of interest is present in the sample.

9. The sensor of claim 1, wherein the first and second electron conducting molecules are different molecules selected from an aromatic compound, a pyridine compound, a polyacetylene polymer, a thiophene compound, an azole compound, a polyaniline polymer or a derivative thereof.

10. The sensor of claim 1, wherein the third electron conducting molecule is an aromatic compound, a pyridine compound, a polyacetylene polymer, a thiophene compound, an azole compound, a polyaniline polymer or a derivative thereof.

11. The sensor of claim 4, wherein the fourth electron conducting molecule is an aromatic compound, a pyridine compound, a polyacetylene polymer, a thiophene compound, an azole compound, a polyaniline polymer or a derivative thereof.

12. The sensor of claim 1, wherein the first probe is DNA, RNA, a protein, an antibody, an antibody fragment that comprises the ability to bind to the biomolecule, an aptamer, an antigen, or an epitope.

13. The sensor of claim 1, wherein the second probe is DNA, RNA, a protein, an antibody, an antibody fragment that comprises the ability to bind to the biomolecule, an aptamer, an antigen, or an enzyme.

14. The sensor of claim 1, wherein the probe molecule of the first probe is directly covalently attached to the first electron conducting molecule.

15. The sensor of claim 1 wherein the probe molecule of the first probe is attached to the first electron conducting molecule via an amine group of the probe molecule.

16. The sensor of claim 1, wherein the first electrode is a metal electrode.

17. The sensor of claim 16, wherein the metal is gold, platinum, or copper.

18. A method for detecting a target of interest, comprising:
    contacting a sensor with a sample that comprises the target, wherein the sensor comprises a first electrode consisting of (i) a first electron conducting molecule; and (ii) a first probe comprising a second electron conducting molecule, wherein the first probe is configured to bind to the target, and wherein the first and second electron conducting molecules are different, the first electron conducting molecule is covalently attached to the first electrode, the first probe is covalently attached to the first electron conducting molecule or the first electrode; and a second electrode consisting of a third electron conducting molecule and a second probe, wherein the second probe does not bind to the target of interest, the third electron conducting molecule is covalently attached to the second electrode or the second probe is covalently attached to the third electron conducting molecule and wherein the third electron conducting molecule is different than the first or second electron conducting molecule;

wherein a first signal is generated when the target binds to the first probe and a second signal is generated without the target binding to the second probe, and wherein detection of the first signal indicates that the biomolecule is present in the sample.

19. The method of claim 18, wherein the first probe is covalently attached to the first electrode.

20. The method of claim 18, wherein the first probe is covalently attached to the first electron conducting molecule.

21. The method of claim 18, wherein the second probe comprises a fourth electron conducting molecule, wherein the fourth electron conducting molecule is the same or different than the third electron conducting molecule.

22. The method of claim 21, wherein the fourth electron conducting molecule is the same as the third electron conducting molecule.

23. The method of claim 18, wherein the sensor further comprises a first flow channel which is in contact with the first electrode and configured such that the sample flows through the first flow channel and the first signal is generated in the first flow channel, and wherein the sensor further comprises a second flow channel which is in contact with the second electrode and configured such that the sample flows through the second flow channel and generates a second signal.

24. The method of claim 23, wherein the sensor further comprises a processor configured to detect the first signal and the second signal.

25. The method of claim 24, wherein the target is detected by comparing a value associated with the first and second signals to a predetermined value, wherein the value associated with the first and second signals being greater than the predetermined value indicates that the target of interest is present in the sample.

26. The method of claim 18, wherein the first and second electron conducting molecules are different molecules selected from an aromatic compound, a pyridine compound, a polyacetylene polymer, a thiophene compound, an azole compound, a polyaniline polymer or a derivative thereof.

27. The method of claim 18, wherein the third electron conducting molecule is an aromatic compound, a pyridine compound, a polyacetylene polymer, a thiophene compound, an azole compound, a polyaniline polymer or a derivative thereof.

28. The method of claim 21, wherein the fourth electron conducting molecule is an aromatic compound, a pyridine compound, a polyacetylene polymer, a thiophene compound, an azole compound, a polyaniline polymer or a derivative thereof.

29. The method of claim 18, wherein the first probe is DNA, RNA, a protein, an antibody, an antibody fragment that comprises the ability to bind to the biomolecule, an aptamer, an antigen, or an epitope.

30. The method of claim 18, wherein the second probe is DNA, RNA, a protein, an antibody, an antibody fragment that comprises the ability to bind to the biomolecule, an aptamer, an antigen, or an epitope.

31. The method of claim 18, wherein the probe molecule of the first probe is directly covalently attached to the first electron conducting molecule.

32. The method of claim 18, wherein the probe molecule of the first probe is attached to the first electron conducting molecule via an amine group of the probe molecule.

33. The method of claim 18, wherein the first electrode is a metal electrode.

34. The method of claim 33, wherein the metal is gold, platinum, or copper.

* * * * *